United States Patent [19]

Marshall, III

[11] 4,266,132
[45] May 5, 1981

[54] APPARATUS FOR CONTROLLING NEUTRONS ESCAPING FROM AN ELEMENTAL ANALYZER MEASURING GAMMA RAYS ARISING FROM NEUTRON CAPTURE IN BULK SUBSTANCES

[75] Inventor: J. Howard Marshall, III, Pasadena, Calif.

[73] Assignee: MDH Industries, Inc., Monrovia, Calif.

[21] Appl. No.: 808,103

[22] Filed: Jun. 20, 1977

[51] Int. Cl.³ .......................... G01N 23/00; G01T 3/00
[52] U.S. Cl. ...................................... 250/359; 250/390
[58] Field of Search ............... 250/358 R, 358 P, 359, 250/390, 391, 392, 432, 435, 453, 518; 313/61 S, 61 D

[56] References Cited

U.S. PATENT DOCUMENTS

| | | | |
|---|---|---|---|
| 3,053,388 | 9/1962 | Tittle | 250/359 |
| 3,676,675 | 7/1972 | Ransohoff et al. | 250/453 |
| 3,778,627 | 12/1973 | Carpenter | 250/518 |

Primary Examiner—Alfred E. Smith
Assistant Examiner—Janice A. Howell
Attorney, Agent, or Firm—Arthur V. Doble

[57] ABSTRACT

In an apparatus for neutron-capture-based on-line elemental analysis of bulk substances, the control of neutrons which escape from the volume in which the analyzed substance is placed improves accuracy and reduces potential radiation hazards. The apparatus includes a neutron source, which exposes the analyzed bulk substance momentarily contained within the instrument to a flux of neutrons. The analyzed substance captures some of these neutrons by (n,γ) reactions, producing prompt gamma rays which are detected to provide the composition measurement. The placement of neutron absorbers around the volume containing the bulk substance and the neutron source and the proper geometrical relationship between the various parts of the instrument provide this neutron control. The materials used in controlling escaping neutrons and in the instrument structure are chosen to avoid interfering radiations. The materials and geometries herein provide neutron control in a manner which does not add significantly to the number of detected background events resulting from the scattering of measured capture gamma rays or from the production of additional gamma rays in the neutron-absorbing materials or in the surrounding structure. Absorbing and controlling escaping neutrons provides fewer neutron interactions in the gamma-ray detector and less scattering of the capture gamma rays, resulting in improved accuracies.

35 Claims, 2 Drawing Figures

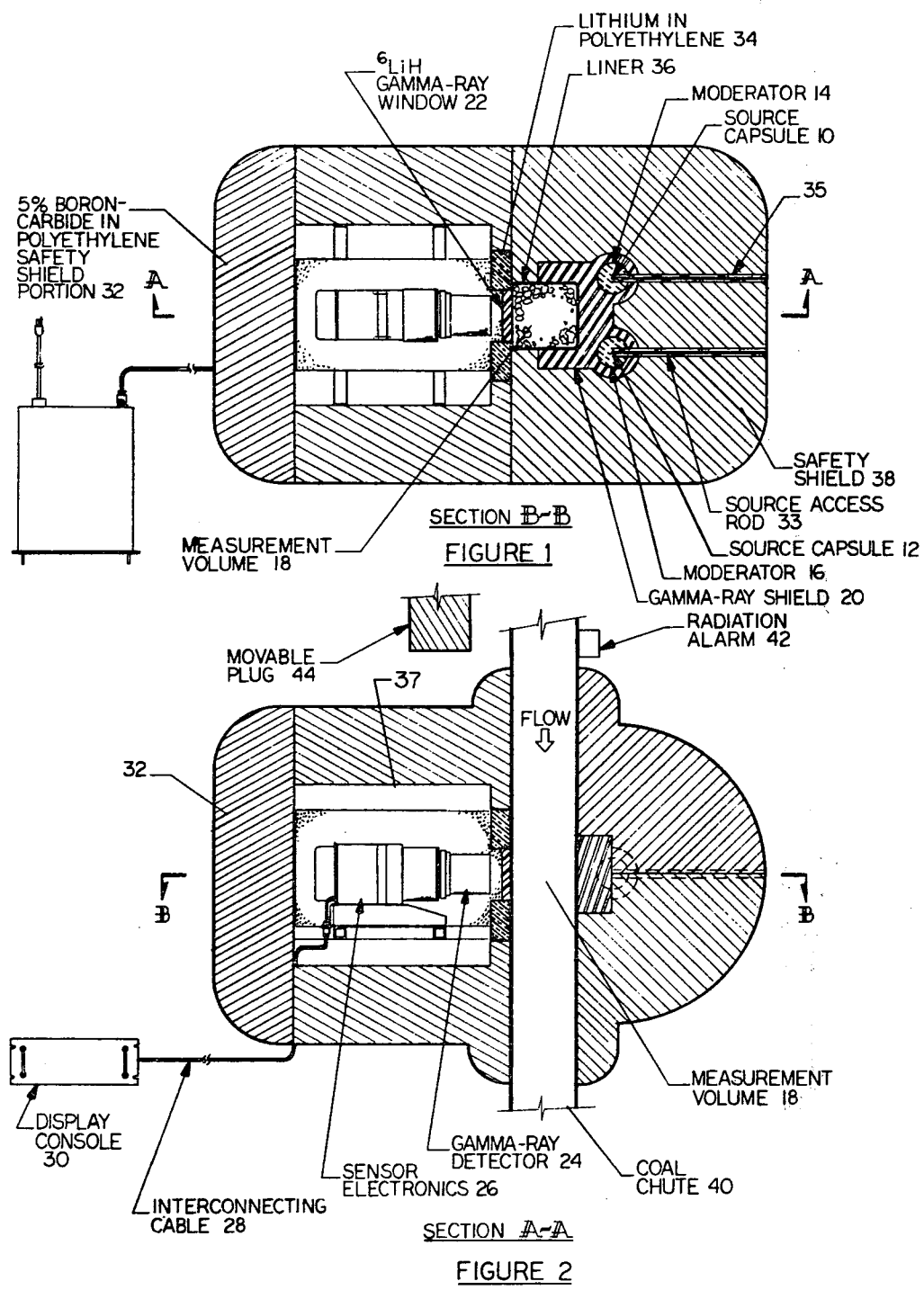

APPARATUS FOR CONTROLLING NEUTRONS ESCAPING FROM AN ELEMENTAL ANALYZER MEASURING GAMMA RAYS ARISING FROM NEUTRON CAPTURE IN BULK SUBSTANCES

BACKGROUND OF THE INVENTION

1. Field of the Invention

This invention generally relates to nuclear meters, and particularly to an apparatus or a method for absorbing and otherwise controlling unwanted escaping neutrons from a neutron-capture-based elemental analyzer for on-line measurement of bulk substances.

2. Description of the Prior Art

The rising cost of fuels, coupled with the need to avoid atmospheric pollution when burning them, has led to the requirement that their composition be known at various points in the fuel-preparation cycle. For example, because of the scarcity of low-sulfur crude oils and the cost of sulfur removal, the value of fuel oil increases significantly as its sulfur content becomes lower, indicating that accurate fuel-oil blending to a fixed sulfur level consistent with allowable amounts of pollution is both cost effective and an efficient utilization of increasingly-scarce hydrocarbons. Furthermore, precise knowledge of the heat content of fuel oil allows furnaces and boilers to be operated in a more efficient manner. In addition, knowledge of the amount of sulfur and other contaminants such as vanadium and nickel in various hydrocarbon streams can help prevent the poisoning of catalysts used in oil refineries, avoiding costly shut downs.

In the case of coal, sulfur content is generally higher than that of oil, making the pollution problem even more severe. As a result, expensive coal-cleaning plants, stack-gas scrubbers and precipitators are necessary, all of which can be operated more efficiently if the coal consumption is known on a real-time, on-line basis. Efficient boiler operation also benefits from this composition measurement, and knowing the composition of the ash in the coal can be used to avoid boiler slagging, which is a costly problem that is generally absent for fuel oil.

Particularly in the case of coal, but also for oil, these composition measurements have to be made on inhomogeneous substances with high mass flow rates and variable compositions. Thus, this measurement should continuously reflect the average composition of the bulk substance, and response times should be fast enough to permit effective process control. Generally the latter requirement implies a speed of response ranging from a few minutes up to an hour.

A technique which can satisfy these requirements can often be used in applications which do not involve fuels or their derivatives. For example, it could measure the nitrogen content of wheat in order to determine the amount of protein present, which in turn is related to food value. Thus, the measurement of fuels is illustrative only and is not essential to this invention, which applies to all measurements of bulk substances by the techniques to be described hereinafter.

Several methods for composition measurement are known in the prior art, the most obvious one being sampling followed by chemical analysis. This technique provides most present data on the composition of various bulk substances. Unfortunately sampling is inherently inaccurate because of the lack of homogeneity of bulk materials, and large continual expenditures for manpower, sampling devices and chemical-analysis equipment are required to provide response times which at best could approach one hour. These disadvantages lead to the consideration of other techniques which are faster, more subject to automatic operations and more of an on-line continuous bulk measurement.

One technique often used in industrial environments for elemental analysis involves X-ray fluorescence. This technique relies on the fact that each atom emits X rays with distinct and well-known energies when external radiations disturb its orbital electrons. Unfortunately, sulfur, which is an interesting element from the standpoints of air pollution and catalyst poisoning, emits mostly 2-keV X-rays, which can only traverse about 0.1 mm of a typical fuel. Iron, which is one of the elements generating the highest-energy X rays in coal, produces mostly a 6-keV X ray, which also cannot escape from any appreciable amount of coal or other nongaseous fuel. Thus, the use of X-ray fluorescence for other than gaseous materials requires either the preparation or the vaporization of a sample in an atmosphere which does not confuse the measurement. In either case, a difficult sampling and sample-preparation problem compounds the errors associated with X-ray fluorescence itself.

A second technique usually involving X rays which are more penetrating is X-ray absorption. In this case one measures the differences in the absorption or scattering of X rays caused by changes in the amounts of certain elements. In the case of relatively-pure hydrocarbons such as refined fuel oil, this technique can provide a useful measurement of sulfur content because sulfur at X-ray energies near 22 keV can have a predominant effect on the X-ray absorption. This predominance, however, is dependent on the lack of most of the metals which are present in coal and may also be present in oil. In addition, 22-keV X rays only penetrate about 2 mm in most non-gaseous fuels, making sampling still a requirement. Moreover, this technique is generally limited to measuring only one of several potentially-interesting elements, and the measurement of the relative amounts of many different elements in a complex mixture such as coal becomes difficult.

Nonetheless, nuclear techniques in general remain attractive because they often can be automated and in principal do not require actual manipulation of the bulk material itself. The problems with X-ray fluorescence and absorption arise partly because the associated radiations are not sufficiently penetrating. However, because the energetic gamma rays produced by the capture of thermal neutrons will penetrate over 100 mm of most fuels, an analysis technique based on them can provide an accurate, continuous, on-line measurement of the elemental composition of bulk substances without sampling.

This technique is based on the fact that almost all elements when bombarded by slow neutrons capture these neutrons at least momentarily and form a compound nucleus in an excited state. Usually the prompt emission of one or more gamma rays with energies and intensities which are uniquely characteristic of the capturing nucleus dissipates most of this excitation energy. Because these prompt gamma rays often have energies in the 2- to 11-MeV range, they can penetrate substantial quantities of material. Thus, for those isotopes with significant capture cross sections and prominent gamma-ray lines, measurement of prompt gamma rays can be used to determine in an on-line, real-time basis the quantity of most of the elements present in bulk substances, which can be flowing through the analyzer.

The above emphasis on thermal neutrons reflects the fact that for most elements the cross section for neutron capture is approximately proportional to the reciprocal of the square root of the neutron energy. Thus, almost all neutron capture occurs at the lowest neutron energies, which happen when the neutrons are in thermal equilibrium with the nuclei of the surrounding medium. As a result, the thermal-neutron-capture cross sections characterize the expected prompt-gamma-ray spectra. These gamma-ray spectra are particularly amenable to simple theoretical interpretation using well-known thermal-neutron-capture cross sections, making automatic operation a feasible concept.

However, because isotopic and other neutron sources generally produce neutrons with average energies of at least several MeV, "moderation" or "thermalization" processes must reduce neutron energies by over eight orders of magnitude in order for them to reach the thermal region near 0.025 eV. Collisions with hydrogen nuclei, which have a mass essentially the same as that of the neutron and a large scattering cross section, are the most effective means for neutron moderation, although collisions with other elements will moderate neutrons to some degree. Because the neutrons move between collisions, the volume of material exposed to significant neutron fluxes can have a considerable extent, which depends mostly on the amount of hydrogen present. Because the thermal neutrons are produced continuously by moderation of the more-energetic neutrons and then diffuse throughout this moderation volume, the substance being measured is sampled over a large extent, providing the bulk measurement.

Although these techniques have been used in the laboratory under controlled conditions, their implementation in an automatic, on-line instrument placed in an industrial environment presents unique problems. One of these problems results from the extended neutron cloud, which provides the bulk measurement. Because the sources of prompt gamma rays follow the flux of thermal neutrons, an extended neutron cloud implies that the gamma rays may have to travel a substantial distance in order to leave the measurement volume and enter an external detector where their energy can be measured. As their path length in the material increases, the probability that they will scatter also increases, decreasing the number of useful events while increasing the unwanted background in the measured gamma-ray spectrum. As a result, the "signal-to-noise ratio" of the measured spectrum decreases, adding to errors and difficulties in automatic data analysis, as well as increasing statistical variations causing larger fluctuations in the measured elemental composition and longer response times. For industrial applications such drawbacks are sufficiently severe that this technique has not been generally used heretofore.

In the prior art, the average gamma-ray path length was longer than that resulting purely from the desire to make a bulk measurement. This added path length resulted from the need to absorb essentially all of the neutrons in the measurement volume in order to prevent escaping neutrons from producing an intolerable background. This background resulted from neutron interactions in the gamma-ray detector itself and from gamma rays produced by neutron capture in materials surrounding the measurement volume.

These difficulties in the prior-art instruments arose partly because materials absorbing escaping neutrons without generating interfering gamma rays were not placed around major portions of the measurement volume. Often iron-containing metals surrounded the measurement volume, and because iron captures neutrons readily, the resulting gamma rays added to the background and to the difficulties in measuring iron in the bulk substance being analyzed. At best those instruments attempted to absorb thermal neutrons entering the gamma-ray detector directly by placing a thin layer of boron around the detector. Unfortunately boron produces a low-energy gamma ray after neutron capture, and this gamma ray added to the background counting rate. As a result, those instruments often had lead mixed with the boron in order to absorb or scatter low-energy gamma rays, but as a result the scattering of the interesting energetic capture gamma rays was also increased, decreasing the signal-to-noise ratio in the measured gamma-ray spectrum. In addition, the boron layer was too thin to absorb any appreciable fraction of the energetic and epithermal neutrons, which represent the majority of the escaping neutrons. Because iodine used in common gamma-ray detectors such as NaI(Tl) or CsI(Na) reacts readily with epithermal neutrons by resonance absorption, the thin boron layer did not remove a significant contributor to the neutron-induced background. Thus, in these prior-art instruments the measurement volume had to be large enough to prevent significant numbers of neutrons from escaping. Because this size was greater than that needed for handling the bulk substance, added gamma-ray scattering reduced instrument accuracy. Additionally a potential radiation hazard to personnel in the vicinity of the instrument existed whenever the measurement volume was empty with the neutron source present.

SUMMARY OF THE INVENTION

If the escaping neutrons are absorbed without producing interfering gamma rays before they can interact in the detector or in uncontrolled materials surrounding the instrument, then the size of the measurement volume can be reduced to levels constrained primarily by material-handling requirements. The applicant herein has conceived of an invention which involves the control of these escaping neutrons through their absorption in a special shielding material interposed between the measurement volume and the detector and in a general shield, which prevents neutron capture in the uncontrolled materials surrounding the instrument and which eliminates radiation hazards to personnel in the vicinity of the instrument. In addition, this invention involves the proper geometrical relationships between the measurement volume, the detector and the general shield, leading to the optimization of the signal-to-noise ratio in the measured energy spectrum from the gamma-ray detector.

The ideal shielding material forming a gamma-ray window to be interposed between the detector and the measurement volume should have the following properties. First, it must have a large cross section for neutron absorption at thermal energies, and a significant value for this cross section should extend to higher energies, particularly to near the iodine resonance at 35 eV. Second, neutron-scattering cross sections should also be large to insure that the neutrons remain within the material for long distances and thus have an increased probability of being absorbed. Third, the atomic weight should be small to provide efficient neutron moderation, which will reduce the energy of fast neutrons to levels where absorption becomes more probable. Fourth, the atomic number and density must be low to prevent excessive scattering and absorption of the capture gamma rays produced by the bulk substance being measured. Fifth, the neutron-absorption reaction in the shielding material should not produce gamma rays or other particles capable of reaching the detector and producing added background. Sixth, the material should be available in the necessary quantities at a reasonable price.

Only a few elements, including $^6$Li and $^{10}$B, do not absorb neutrons predominantly by $(n,\gamma)$ reactions, which often result in energetic gamma rays adding substantially to the background. Although $^{10}$B undergoes a $(n,\alpha)$ reaction, the resulting $^7$Li nucleus is excited and emits a 0.48-MeV gamma ray. These gamma rays can add to the low-energy counting rate, as discovered in the prior art, and compound the problems with pulse pileup and dead time. On the other hand, the $^6$Li$(n,\alpha)^3$H reaction produces only charged particles with very-short ranges, virtually eliminating any background produced by the shielding material. Only one $^6$Li nucleus in 21,000 reacts with neutrons by $^6$Li$(n,\gamma)^7$Li, to produce gamma rays from 2.61 MeV to 7.26 MeV.

Unfortunately, the common lithium isotope, $^7$Li, is nearly inert to neutrons and comprises 92.6% of natural lithium. However, isotopically-separated 95% $^6$Li is available at a price which is not so large as to prohibit its use in the gamma-ray window or as a minor constituent in a lithium compound used in the general shield. Lithium-six has a neutron-absorption cross section of $9.45 \times 10^{-26}$ m$^2$ at thermal energies, and this cross section exceeds $10^{-27}$ m$^2$ up to energies above 100 eV, illustrating the effectiveness of $^6$Li in absorbing both thermal and epithermal neutrons. However, its scattering cross section is rather small compared to hydrogen, indicating that the path lengths for energetic neutrons in pure $^6$Li will be considerably shorter than those in hydrogenous materials. Thus, it is reasonable to combine the good neutron-absorption properties of $^6$Li with the good scattering and moderating properties of $^1$H by using lithium-hydrogen compounds as the shielding material. Such compounds often have low density and atomic number, which results in a minimal disturbance of the interesting capture gamma rays.

The simplest such compound is $^6$LiH, which is a crystalline powder with reasonable chemical properties, such as a high heat of decomposition (689° C.), although it must be protected from moist air to avoid deterioration. This compound has a density of 0.68 g/cm$^3$ and is easily fabricated from lithium metal. A thickness of about 30 mm of $^6$LiH will decrease neutron currents substantially for energies below 1 keV, reducing the probability for neutron interactions in the detector and permitting the reduction of the probability of scattering of interesting gamma rays by decreasing the size of the measurement volume.

However, if a good neutron absorber such as $^6$LiH is interposed between the surface of the measurement volume and the detector and then the measurement volume is decreased accordingly, more neutrons will escape from other parts of the surface of the measurement volume, potentially producing capture gamma rays adding to the background. Thus, an appropriate general shield must surround the measurement volume, and this shield must not add to the gamma-ray or neutron-induced background. In addition, in an industrial environment the measurement volume might empty, causing a severe radiation hazard to personnel near the instrument unless the general shield is also an effective safety shield. Furthermore, if the neutron source is not placed inside the measurement volume, then such a safety shield is also necessary to prevent a radiation hazard during normal operation.

Similar requirements apply to the choice of materials for the general safety shield as apply to the materials for the gamma-ray window, and the use of $^6$LiH or other $^6$Li-hydrogen compounds can provide satisfactory performance, although their cost may be prohibitive because of the large mass of the general safety shield. However, here low scattering of interesting capture gamma rays is not important, because gamma rays traveling through this part of the shield usually do not enter the detector. Thus, the safety shield generally can be denser and thicker than the gamma-ray window, permitting lower concentrations of lithium-six, even possibly to the extent of using much-cheaper natural lithium. Furthermore, low-energy gamma rays produced in the parts of the shield which are far removed from the detector or which have substantial quantities of material intervening between them and the detector have only a low probability of reaching the detector. Thus, some parts of the shield can also contain natural boron, which is considerably cheaper than lithium-six. Because all such shielding materials usually contain hydrogen in order to moderate fast neutrons, typical materials for the general shield are polyethylene, paraffin, water, stearates, and wax, any of which may be loaded with boron or lithium compounds.

Usually these shielding compounds do not have proper mechanical properties to contain the substance being analyzed, which may be hot, abrasive and corrosive, as well as flowing at high rates. Thus, the general safety shield often must contain a structural material which lines the measurement volume and contains the analyzed bulk substance. Such structural materials generate two types of problems because they are often exposed to relatively-high neutron fluxes. For those materials which contain only elements whose concentration in the bulk substance being analyzed is not to be measured, gamma rays from neutron capture simply add to the general background. If, however, the structural material contains an interesting element, additional errors may arise in the measurement of the amount of this element, because the instrument often cannot tell if its gamma rays come from the analyzed substance or from the structure.

Thus, the structural materials should be as thin as possible and should contain in appreciable quantities only those elements with a low cross section for $(n,\gamma)$ reactions. In addition, the major elements therein should not be elements being measured in the bulk substance in the measurement volume.

Common structural materials include various steels, which contain iron and other elements with large neutron-capture cross sections producing many energetic gamma rays. Although steel was commonly used for the liner of the measurement volume in prior-art instruments, it generally produces an unacceptable background in the measured energy spectrum, particularly if iron is an element being analyzed.

Better choices for the measurement-volume liner are aluminum, magnesium, and zirconium, all of which have a much-smaller neutron-capture cross section than iron. Care must be taken, however, in the choice of the specific alloys used, because small quantities of many alloying metals can be more significant than the basic metal itself. However, usable alloys exist for all of these metals, making them possible choices for the liner of the measurement volume, with the best choice usually depending on the elements being measured.

Acceptable aluminum alloys are commonly available, but aluminum has the highest neutron-capture cross section of these elements, and its concentration can be of interest for fuels such as coal. Magnesium has the lowest capture cross section, although acceptable alloys from the standpoints of spectral interference, strength and ease of fabrication are limited. Even though the magnesium concentration in bulk substances such as coal may be interesting, its low capture cross section often makes its accurate measurement impossible, indicating that its use as a structural material in that case will not detract from inherent instrument accuracy. Although zirconium has a higher capture cross-section than magnesium, it is seldom an interesting element for measurement, making it a good choice if magnesium and aluminum are unacceptable.

If the bulk substance in the measurement volume corrodes the structural material, then a thin chemically-inert coating of such a material as polytetrafluoroethylene, polyethylene or polycarbonate can protect the main structural material. If the coating material is thin enough, it will add negligibly to measurement errors even if it contains elements of interest. In addition, measurement of the number of gamma rays produced by the basic structural material can be used to correct for the coating elements, because both materials are exposed to essentially the same neutron fluxes and have basically the same geometrical relationship to the detector and other parts of the instrument.

Several geometrical principles can also be used to reduce background induced by escaping neutrons. For example, those neutrons which succeed in penetrating the gamma-ray window and entering the detector must be allowed to escape from the detector freely. Otherwise, if these neutrons are scattered back and forth through the detector by placing neutron-scattering materials, such as the general safety shield, too close to the detector, their probability of interacting in the detector increases, adding to the background.

Furthermore, because most of the neutrons which escape from the surface of the measurement volume scatter several times before reaching its surface, they leave the surface with random directions of motion. On the other hand, the interesting, detected gamma rays from neutron-capture reactions in the measurement volume mostly come directly from a volume nearer the neutron source. As a result, moving the detector away from the surface of the measurement volume decreases the probability that a neutron reaches the detector faster than it decreases the probability for gamma-ray detection, improving the signal-to-noise ratio from this effect. Furthermore, because neutrons are unlikely to scatter back and forth between the detector and the surface of the gamma-ray window when they are widely separated, in this case the neutron current density rather than the flux provides the better estimate of the number of neutrons entering the crystal, reducing the relative importance of low-energy neutrons where absorption cross sections are largest.

The present invention has several features of novelty over the known prior art, including the use of specific materials and geometrical arrangements to absorb and otherwise control neutrons escaping from the measurement volume of an on-line elemental analyzer detecting neutron-capture gamma rays and to perform this neutron absorption and control in such a manner as to optimize the signal-to-noise ratio in the measured energy spectrum, permitting accurate, automatic operation suitable for industrial environments.

It is an object of this invention to provide an improved apparatus for absorbing and otherwise controlling neutrons escaping from a neutron-capture-based meter for elemental analysis of bulk substances.

It is another object of this invention to provide an improved neutron absorber placed between a gamma-ray detector and a bulk substance producing gamma rays upon neutron capture.

It is a further object of this invention to add to the neutron absorbers used in a neutron-capture-based meter a neutron moderator in order to enhance the absorption of energetic and epithermal neutrons.

It is also an object of this invention to absorb escaping neutrons in a manner that does not add significantly to the number of background events in the measured energy spectrum from the gamma-ray detector.

It is an additional object of this invention to attenuate in an improved manner escaping radiation from a neutron-capture-based meter in order to avoid a radiation hazard to personnel in the vicinity of the meter.

It is another object of this invention to improve the signal-to-noise ratio in the measured energy spectrum from the gamma-ray detector in a neutron-capture-based meter for elemental analysis of bulk substances by reducing the size of the measurement volume and absorbing the escaping neutrons resulting therefrom.

For a better understanding of the present invention, together with other and further objects thereof, reference is made to the following description taken in connection with the accompanying drawings in which preferred embodiments of the invention are illustrated, the scope of the invention being pointed out and contained in the appended claims.

BRIEF DESCRIPTION OF THE DRAWINGS

FIG. 1 shows a cross-sectional view of the shielding and other structure associated with a meter for the elemental analysis of coal, which forms a preferred embodiment of this invention.

FIG. 2 shows further details of the same instrument as that shown in FIG. 1, but in this case the section view has been taken along the line A—A in FIG. 1. The line B—B of FIG. 2 shows the sectioning line used for producing FIG. 1.

DESCRIPTION OF THE PREFERRED EMBODIMENTS

The application of these methods to the elemental analysis of coal forms one of the preferred embodiments of this invention, as shown in FIGS. 1 and 2. Other embodiments involve the on-line measurement of coal-water mixtures, coal-oil mixtures, crude oil, fuel oil, gasoline, wheat and most other bulk substances containing some hydrogen. Thus, the portions of the preferred embodiment shown in FIGS. 1 and 2 which are specific to the measurement of coal are illustrative only and are not intended to limit the scope of this invention.

The instrument includes means for containing the bulk substance to be analyzed, which may flow through the instrument in order to provide a continuous, on-line measurement of bulk composition. In the embodiment shown in FIGS. 1 and 2, this means consists of the centrally-located measurement volume 18, in which the coal being analyzed is confined. Measurement volume 18 is the region throughout which the composition measurement takes place. Coal passing through the coal chute 40 continuously fills the measurement volume 18 with a current coal sample, facilitating the desired continuous, on-line bulk measurement.

The instrument also includes means for providing a source of neutrons. In the embodiment shown in FIG. 1, said means consist of two capsules 10 and 12 containing the isotope californium-252. In other embodiments of this invention the source could contain different isotopes, such as plutonium mixed with beryllium, or could contain a neutron generator, such as that using the $^3H(d,n)^4He$ reaction. Additionally the instrument could contain one or several neutron sources, which could all be the same type or could be various combinations of source types. The neutron-producing means can be located either outside of the volume containing the bulk substance to be analyzed, as shown in FIGS. 1 and 2, or within this volume. If several neutron sources are present, some of these sources may be within this measurement volume, while other sources are external thereto. The principles forming a part of this invention apply to all of these variations of the embodiment shown in FIGS. 1 and 2.

In this embodiment neutron moderators 14 and 16 surround the source capsules 10 and 12 in order to reduce neutron energies before the neutrons enter the measurement volume 18. A gamma-ray shield 20 then surrounds the moderators 14 and 16 to absorb gamma rays produced by the source and the moderators and to provide a material with low neutron absorption through which neutrons can diffuse away from the source. The use of the moderators and gamma-ray shield is also not essential to this invention, and their use in the embodiment shown in FIGS. 1 and 2 is not intended to limit the scope of the invention.

Some neutrons will diffuse through the gamma-ray shield 20 into the measurement volume 18. There hydrogen present in the coal being analyzed will moderate them further, and then they often will be captured by the various nuclei present in the analyzed coal. These neutron-capture reactions generally produce gamma rays, which travel outward in all directions. Some of these gamma rays will travel through the measurement volume 18 and the neutron-absorbing gamma-ray window 22 and enter the gamma-ray detector 24 shown in FIG. 2.

In the preferred embodiment shown in FIGS. 1 and 2, this detector 24 is a large NaI(Tl) crystal, although other detectors such as CsI(Tl), CsI(Na), Ge or Ge(Li) could be used in instruments incorporating the features of this invention. The invention also is not limited to the case of a single gamma-ray detector, as shown in FIGS. 1 and 2, and the principles of the invention apply equally well to instruments containing several detectors, which may be all the same type or a combination of types.

When the gamma rays interact in the gamma-ray detector 24, they produce electrical signals indicative of their energy. The sensor electronics 26 convert these electrical signals into digital information, which is transmitted over an interconnecting cable 28 to the display console 30. The display console 30 processes this information using the fact that neutron capture produces an energy spectrum which depends on the amounts of the various elements capturing the neutrons. The result of this processing is information concerning the relative concentrations of the various elements of interest in the measurement volume 18 and any other properties, such as density, which may be usefully obtained from the measured spectrum. The interface between the sensor electronics 26 and the display console 30 and the methods used therein do not form a part of this invention.

Although the neutrons which the bulk substance in the measurement volume 18 captures provide the useful information, many neutrons are not captured there and could potentially escape from the instrument or could interact in the gamma-ray detector 24. In the preferred embodiment shown in FIGS. 1 and 2, the neutron sources 10 and 12 are outside of the measurement volume 18, indicating that most neutrons will not enter the measurement volume 18. Even in other embodiments wherein the neutron source is contained within the measurement volume, the minimization of the distance traveled by the interesting capture gamma rays usually results in many neutrons still escaping from the measurement volume. Failure to absorb these unused neutrons would result in a radiation hazard, particularly if the measurement volume 18 were empty, and their capture in nearby structural materials would produce energetic gamma rays adding to the background. In addition neutron interactions in the gamma-ray detector 24 generally produce background signals.

This invention includes several features for controlling these unused escaping neutrons in a manner that avoids substantial increases in the background portions of the measured energy spectrum. One of these features comprises a means for absorbing neutrons which are not captured by the bulk substance being analyzed. In the embodiment shown in FIGS. 1 and 2, this neutron-absorbing means includes the $^6LiH$ gamma-ray window 22, the boron-dopedpolyethylene safety shield 32 and 38 with the source access rods 33 and 35, the lithium in polyethylene 34 and the liner 36 for the measurement volume 18. Although in this embodiment the means for containing the bulk substance being analyzed becomes a part of the neutron-absorbing means, this commonality of function is not necessary for the implementation of the principles of this invention. This invention does include, however, several aspects of the overall geometrical relationship between the various parts of the instrument as specifically described hereinafter.

The safety shield 38 must attenuate source gamma rays, epithermal neutrons, thermal neutrons and capture gamma rays. Because the gamma-ray shield 20 can reduce the dose from source gamma rays by over a factor of 10, neutron attenuation becomes a principal task for the safety shield 38. Because many of the neutrons leaving the moderators 14 and 16 are still energetic, the safety shield must contain a hydrogenous material to reduce the neutron energies to the region where capture is probable. Although hydrogen will also capture thermal neutrons, a penetrating 2.23-MeV gamma ray results, and these capture gamma rays represent a radiation hazard, a potential source of background counts in the detector and a signal which can be confused with that from hydrogen in the bulk substance being measured. Thus, an element which does not produce energetic capture gamma rays should be added to the hydrogenous material in an amount which overwhelms the neutron capture by hydrogen.

A reasonably-priced hydrogenous material with good structural properties is polyethylene, although other materials, such as water, water-extended polyester and concrete, can also be used. Thus, for those portions 32 of the safety shield 38 which are not near the detector 24, 5% of natural boron-carbide can be mixed with the polyethylene in order to capture all but about 2% of the thermal neutrons in boron. Because boron captures neutrons by the short-range charge-particle-producing $^{10}B(n,\alpha)^7Li^*$ reaction, with the excited $^7Li$ nucleus giving off only a low-energy (0.48-MeV) gamma ray, natural boron produces a low dose rate from capture gamma rays. Furthermore, such low-energy gamma rays are unlikely to be able to penetrate through the shield 32 and the measurement volume 18 to reach the detector 24 and add background counts. Finally, because natural boron contains 19% $^{10}B$, isotopically-separated boron is usually not necessary, resulting in the cost of the boron-carbide being nearly insignificant.

The portions 32 of the safety shield 38 containing 5% boron carbide in polyethylene can extend behind the source capsules 10 and 12 and along the sides of the measurement volume 18 which do not face the detector 24. Because the shielding near the detector 24 should not emit the 0.48-MeV gamma rays arising from neutron capture by boron, boron doping should not be used close to the detector 24. In the preferred embodiment shown in FIGS. 1 and 2, these portions 22 and 34 of the shield used lithium doping. Lithium doping could also be used in other portions 32 of the safety shield 38 where in the preferred embodiment boron doping was used, with cost considerations being the primary basis for choosing between boron and lithium doping in these portions 32 of the safety shield 38. A combination of lithium and boron doping also constitutes a part of this invention.

The gamma-ray window 22 placed between the front of the detector 24 and the measurement volume 18 must absorb thermal and epithermal neutrons effectively without producing capture gamma rays, which, because of their production close to the detector, would have a high probability of reaching the detector and adding to the background. In the preferred embodiment shown in FIGS. 1 and 2, $^6LiH$ formed the gamma-ray window 22 and provided this interference-free neutron attenuation. Without this material or one of similar properties, the measurement volume 18 would have had to be considerably larger, reducing the signal-to-noise ratio of the measured energy spectrum as a result of scattering of the capture gamma rays.

Although a material such as $^6LiH$ could be placed along the entire wall of the measurement volume 18 which faces the detector 24, the cost of the resultant amount of lithium which has been enriched in lithium-six could be excessive. Fortunately for those parts of the shield which are not in the path of most of the capture gamma rays from the measurement volume 18, the shield can be thicker, permitting a substantial reduction in the amount of lithium used, because the added moderator will reduce the neutron energies to the region of large capture cross sections.

In the preferred embodiment, lithium in polyethylene 34 was used for this portion of the shield and the use of natural lithium and the use of lithium which has been enriched in lithium-six for this doping constitute a part of this invention. Also the basic material can be any hydrogeneous substance such as polyethylene, stearates, paraffin, wax and water. If the lithium-six comprises 2% by weight in polyethylene with a hydrogen density of 0.1 g/cm$^3$, then the lithium will capture about 99% of the neutrons, reducing the background from gamma rays from neutron capture by hydrogen to a negligible level. This reduction of such interfering gamma rays produced near the detector is an important aspect of controlling neutrons escaping from the measurement volume 18.

The liner 36 for the measurement volume 18 is another potential source of interfering gamma rays. This material must have the proper chemical and structural properties to contain the bulk substance being analyzed, but also it must not produce gamma rays which interfere with measured elements or add substantially to the background. In the preferred embodiment of FIGS. 1 and 2 for the measurement of low-ash coal, the measurement accuracy for magnesium was not good enough to be useful, and as a result it became an "uninteresting" element as far as that meter was concerned. Then its low capture cross section became a distinct advantage in preventing high background counting rates.

The use of magnesium presented two problems. First, because pure magnesium is structurally weak, some metal or metals had to be alloyed with it to provide reasonable mechanical properties. Small quantities of usual alloy metals such as aluminum, manganese or copper could produce unacceptable background and interference problems. Second, because magnesium is a relatively reactive metal, it may corrode excessively in a coal stream, although this problem is less severe for dried coal than for coal slurries.

Fortunately the liner 36 does not need to be very strong, because the coal chute 40 is vertical and furthermore the shielding materials behind it can accept most compressional loads. In addition magnesium-zirconium alloys exist which are quite strong and produce minimal interferences, because zirconium also has a low neutron-capture cross section and is not found in measurable quantities in coal.

If corrosion or wear become problems, the magnesium alloy can be coated with polytetrafluoroethylene or an organic compound such as polyethylene, and such a coating is resistant to wear and chemical attack. In order to be safe with regard to wear and corrosion, the instrument design permits the liner 36 to be easily removed. Thus, replacement of a damaged liner 36 is not a major effort.

Magnesium is not the only material which can be used for the liner 36 of the measurement volume 18 in various embodiments of this invention. Some other metals, such as aluminum and zirconium, also have low neutron-capture cross sections and could be used under some circumstances or in regions without high neutron fluxes. Even various steels, such as stainless steel, can be used if they are thin enough or if iron is not an interesting element. Finally various organic compounds, such as polycarbonate, rubber and neoprene, are usable whenever their carbon and hydrogen interference either has no consequence or can be subtracted with sufficient accuracy. Corrections for such interferences can often be based on the measurement of an element which is generally only in the structure and is exposed to the same neutron fluxes as those entering the material for which the correction is being made.

Several geometrical considerations are also important in controlling escaping neutrons. For example, as shown in FIGS. 1 and 2, the detector 24 can be removed from the surface of the gamma-ray window 22, attenuating neutron interactions in the detector faster than detected gamma rays. In addition, the shielding should not be placed directly against the detector 24, because the detector 24 should be generally free from materials which could reflect epithermal neutrons back into it. Otherwise those faster neutrons which escape from the measurement volume 18 can be scattered back and forth through the detector 24, causing unacceptable background counting rates from resonance capture by iodine or from other neutron reactions. Finally the sensor electronics 26 should be near the detector 24 in order to preserve fast pulses and good temperature stability, which are important for accurate operation.

A further constraint arises from the need to avoid a radiation hazard if the measurement volume 18 is empty. In that case neutrons will not be absorbed by the bulk substance being analyzed and will leave the measurement volume 18 at the detector 24 side. Thus, enough shielding must be placed there in order to absorb these escaping neutrons, but this shielding must not cause added background in the measured energy spectrum when the measurement volume 18 is full.

One solution to this problem is that shown in FIGS. 1 and 2. There the shielding on the detector side of the measurement volume 18 has been placed behind the sensor electronics 26 such that the detector 24 and the sensor electronics 26 are located within a chamber 37 in the neutron-absorbing means. Even in this configuration some scattered radiation can leave the top and the bottom of the coal chute 40 passing through the measurement volume 18 when it is empty, because this region is not covered by shielding. Because the placement of shielding in this region is constrained by equipment used to move coal into and out of the instrument, this embodiment of the invention did not include any shielding in these regions. Because the scattered radiation is low, and because these regions are unoccupied, no shielding here was necessary. A radiation alarm 42 and/or a movable plug 44 for the coal chute 40 when no coal is present are other possible solutions to the shielding problem when the coal chute is empty and constitute a part of this invention. A plug has the advantage of also calibrating the instrument if it closely simulates the bulk substance being analyzed.

What I claim as new is:

1. An improved apparatus for the on-line analysis of the composition of a bulk substance, wherein said analysis includes the production and capture of neutrons and the detection of the resulting capture gamma rays, said apparatus comprising, in combination:
   (a) means for containing the bulk substance to be analyzed;
   (b) neutron-producing means for providing neutrons, which generate gamma rays by neutron-capture reactions with the nuclei in the bulk substance being analyzed, the neutron-producing means being operably associated with the means for containing the bulk substance;
   (c) a gamma-ray detector operably associated with the neutron-producing means and the means for containing the bulk substance being analyzed, the gamma-ray detector producing electrical signals indicative of the gamma-ray energies to provide for the measurement of the energy spectrum of the capture gamma rays; and
   (d) means for absorbing neutrons emitted by the neutron-producing means which are not captured by the bulk substance being analyzed, the neutron-absorbing means comprising compounds which are placed outside of the means for containing the bulk substance being analyzed and which attenuate the flux of uncaptured neutrons without producing or scattering significant numbers of gamma rays which reach the gamma-ray detector;
   whereby the measurement accuracy of the apparatus is improved and radiation hazards are reduced.

2. The apparatus of claim 1, above, wherein the neutron-absorbing means further comprises the means for containing the bulk substance to be analyzed.

3. The apparatus of claim 2, above, wherein the neutron-absorbing means further comprises a liner on the surface of the means for containing the bulk substance being analyzed to prevent its leakage from the apparatus, the liner having the property of not producing a large background in the energy spectrum measured by the gamma-ray detector or interference with analyzed elements in the bulk substance.

4. The apparatus of claim 3, above, wherein said liner comprises magnesium.

5. The apparatus of claim 3, above, wherein said liner comprises aluminum.

6. The apparatus of claim 3, above, wherein said liner comprises zirconium.

7. The apparatus of claim 3, above, wherein said liner comprises polytetrofluoroethylene.

8. The apparatus of claim 3, above, wherein said liner comprises an organic material, said organic material comprising principally the elements hydrogen, carbon and oxygen.

9. The apparatus of claim 3, above, wherein said liner is coated with a thin, chemically-inert layer which is not corroded rapidly by the bulk substance in the measurement volume.

10. The apparatus of claim 3, above, wherein the liner comprises in combination an element which is not in the bulk substance being analyzed and an element which is present therein, the measurement of the quantity of the signal from the element not present in the bulk substance being used to correct for the signal from the element which is present in the bulk substance;
    whereby errors in the measurement of an element which is present both in the liner and in the bulk substance being analyzed can be reduced.

11. The apparatus of claim 3, above, wherein said liner is easily removable whereby damage to the liner can be repaired.

12. The apparatus of claim 1, above, wherein said neutron-absorbing means comprises a gamma-ray window located adjacent to the means for containing the bulk substance to be analyzed, said gamma-ray window being positioned with respect to the gamma-ray detector to enable gamma rays produced within the bulk substance being analyzed to reach the gamma-ray detector without a substantially-increased probability of having their energy degraded through scattering;
    whereby the ratio of the number of undegraded capture gamma rays to the number of neutrons entering the gamma-ray detector is increased.

13. The apparatus of claim 12, above, wherein the neutron-absorbing means further comprises compounds surrounding the edges of the gamma-ray window, the compounds absorbing uncaptured, escaping neutrons in the vicinity of the gamma-ray window;
    whereby the number of neutrons entering the gamma-ray detector and the number of gamma-rays entering the gamma-ray detector produced by neutron capture in surrounding materials are reduced.

14. The apparatus of claim 1, above, wherein the neutron-absorbing means comprises a safety shield enclosing the neutron-producing means and the means for containing the bulk substance to be analyzed, said safety shield preventing the escape of neutrons into the region surrounding the instrument;

whereby a radiation hazard to personnel in the vicinity of the instrument and a background in the energy spectrum measured by the gamma-ray detector caused by gamma rays resulting from neutron capture in surrounding materials are avoided.

15. The apparatus of claim 14, above, wherein the means for absorbing neutrons further comprises a rod within the safety shield to provide access to the neutron-producing means without disassembly of the apparatus.

16. The apparatus of claim 1, above, wherein the means for absorbing neutrons comprises the isotope lithium-six.

17. The apparatus of claim 16, above, wherein the relative amount of lithium-six compared to other lithium isotopes has been enriched with respect to its natural abundance;

whereby the mass of the neutron-absorbing compound is reduced, minimizing the scattering of gamma rays.

18. The apparatus of claim 16, above, wherein the compounds containing lithium-six also contain hydrogen;

whereby the neutron energies are rapidly reduced, enhancing the absorption of energetic and epithermal neutrons.

19. The apparatus of claim 18, above, wherein the compound containing lithium-six and hydrogen comprises lithium hydride.

20. The apparatus of claim 19, above, wherein the relative amount of lithium-six compared to other lithium isotopes has been enriched with respect to its natural abundance.

21. The apparatus of claim 20, above, wherein the lithium hydride which has been enriched in lithium-six forms a shield between the gamma-ray detector and the bulk substance being measured;

whereby neutrons escaping toward the detector are absorbed without producing a large gamma-ray background from either neutron capture or the scattering of gamma rays produced in the bulk substance.

22. The apparatus of claim 18, above, wherein the compound containing lithium-six and hydrogen comprises lithium mixed with polyethylene.

23. The apparatus of claim 18, above, wherein the compound containing lithium-six and hydrogen comprises lithium-six stearate.

24. The apparatus of claim 1, above, wherein the means for absorbing neutrons comprises the isotope boron-ten.

25. The apparatus of claim 24, above, wherein the relative amount of boron-ten compared to other boron isotopes has been enriched with respect to its natural abundance.

26. The apparatus of claim 24, above, wherein the compounds containing boron-ten also contain hydrogen;

whereby the neutron energies are rapidly reduced, enhancing the absorption of energetic and epithermal neutrons.

27. The apparatus of claim 26, above, wherein the compounds containing boron-ten and hydrogen comprise boron carbide mixed with polyethylene.

28. The apparatus of claim 26, above, wherein the compounds containing boron-ten and hydrogen comprise boric acid mixed with water.

29. The apparatus of claim 1, above, wherein the means for absorbing neutrons is placed sufficiently far away from the gamma-ray detector that escaping neutrons are not likely to be scattered back and forth through the detector, whereby neutron scattering in the means for absorbing neutrons does not increase significantly the probability that the neutrons interact in the detector, avoiding the resultant background interfering with the gamma-ray measurement.

30. The apparatus of claim 29, above, wherein the gamma-ray detector is located within a chamber in the means for absorbing neutrons.

31. The apparatus of claim 1, above, wherein the gamma-ray detector is not placed directly against the means for containing the bulk substance to be analyzed or the means for absorbing neutrons, whereby the ratio of the number of capture gamma rays to the number of neutrons entering the gamma-ray detector is increased.

32. The apparatus of claim 1, above, further comprising a means for providing an alarm if radiation levels become excessive;

whereby personnel in the vicinity of the instrument can avoid dangerous radiation doses.

33. The apparatus of claim 1, above, further comprising means for preventing excessive radiation levels when the bulk substance to be analyzed is not present, the means for preventing excessive radiation levels being movable into a position to block the flow of the bulk substance into the means for containing the bulk substance to be analyzed.

34. The apparatus of claim 33, above, wherein the means for preventing excessive radiation levels comprises a movable plug which can be inserted into the means for containing the bulk substance to be analyzed.

35. The apparatus of claim 34, above, wherein the movable plug comprises materials used to measure the response of the instrument to known conditions;

whereby the instrument can be calibrated.

* * * * *